United States Patent
Angres et al.

(10) Patent No.: US 6,890,941 B1
(45) Date of Patent: May 10, 2005

(54) COMPOSITIONS CONTAINING HMG CO-A REDUCTASE INHIBITORS AND POLICOSANOL

(75) Inventors: Isaac A. Angres, North Potomac, MD (US); Ruben Minski, Barranquilla (CO); Meyer Minski, Golden Beach, FL (US)

(73) Assignee: Procaps S.A., Barranquilla (CO)

( * ) Notice: Subject to any disclaimer, the term of this patent is extended or adjusted under 35 U.S.C. 154(b) by 0 days.

(21) Appl. No.: 10/725,405

(22) Filed: Dec. 3, 2003

(51) Int. Cl.[7] .................. A61K 31/44; A61K 31/40; A61K 31/35; A61K 31/225; A61K 31/045
(52) U.S. Cl. .................. 514/345; 514/419; 514/423; 514/460; 514/548; 514/724
(58) Field of Search .................. 514/345, 419, 514/423, 460, 548, 724

(56) References Cited

U.S. PATENT DOCUMENTS

| | | | | |
|---|---|---|---|---|
| 4,744,988 A | * | 5/1988 | Brox | .................. 424/456 |
| 5,856,316 A | * | 1/1999 | Laguna Granja et al. | ... 514/164 |
| 2003/0232796 A1 | * | 12/2003 | Cooper et al. | .............. 514/169 |

OTHER PUBLICATIONS

Medline Abstract, Moroyama et al. Current Drug Targets. Cardiovascular & haematological disorders (2004 Mar) 4 (1) 35 52.*
Medline Abstract, Illingworth, Cardiology (1989), 76 Suppl 1 83–94; discussion 94–100.*

* cited by examiner

*Primary Examiner*—Raymond J. Henley, III
(74) *Attorney, Agent, or Firm*—Isaac A. Angres

(57) ABSTRACT

The present invention provides pharmaceutical compositions, methods, combinations, and kits for treating a disorder related to elevated serum cholesterol concentration, for example, hypercholesterolemia, atherosclerosis, elevated LDL plasma levels, low HDL plasma levels, hypertriglyceridemia, hyperlipidemia, hypertension, cholesterol gallstones, and lipid storage diseases. The compositions, methods, combinations, and kits of the present invention are pharmaceutical compositions comprising atherapeutically effective amount of a lipid regulating agent, such as a HMG-CoA reductase inhibitor, and compound that inhibits cholesterol synthesis at a point between the formation of acetate and mevalonate. A typical pharmaceutical composition of the invention contains and effective amount of atorvastatin and an effective amount of policosanol.

24 Claims, No Drawings

# COMPOSITIONS CONTAINING HMG CO-A REDUCTASE INHIBITORS AND POLICOSANOL

FIELD OF THE INVENTION

The present invention relates to methods of treating cardiovascular diseases, and specifically relates to combinations of compounds, compositions, and methods for their use in to medicine, particularly in the prophylaxis and treatment of hyperlipidemic conditions such as are associated with atherosclerosis, hypercholesterolemia, and other coronary artery disease in mammals.

The instant invention is also directed to new pharmaceutical compositions useful as hypocholesterolemic and hypolipidemic agents. The present invention also relates to a combination of a cholesterol biosynthesis inhibitor and a compound that inhibits cholesterol synthesis at a point between the formation of acetate and mevalonate which combination is useful in reducing plasma cholesterol. More particularly, this invention concerns compositions containing: (1) certain inhibitors of the enzyme 3-hydroxy-3-methylglutaryl-coenzyme A reductase (HMG-CoA reductase); and (2) policosanol. The invention also relates to a method of lowering blood serum cholesterol levels and modulating blood serum lipid levels employing such pharmaceutical compositions.

This invention also relates to stable soft gelatine capsules (hereinafter softgel) containing HMG-CoA reductase inhibitors and policosanol. The present invention also features soft gelatin capsules with a gelatin shell, at least one plasticizer and a capsule filling which contains at least a combination of HMG-CoA reductase inhibitors and policosanol, as well as processes for their manufacture.

The invention further relates to methods of reducing plasma cholesterol levels and treating or preventing atherosclerosis comprising administering an effective amount of a combination of a HMG-CoA reductase inhibitors and policosanol.

The present invention also describes a method for preventing, stabilizing or causing regression of atherosclerosis in mammalian species by administering a combination of a cholesterol lowering drug, such as an HMG CoA reductase inhibitor, for example, atorvastatin, and policosanol and to a pharmaceutical combination for use in such method.

BACKGROUND OF THE INVENTION AND DESCRIPTION OF THE PRIOR ART

Atherosclerosis (or arteriosclerosis) is the term used to describe progressive narrowing and hardening of the arteries that can result in an aneurysm, thrombosis, ischemia, embolism formation or other vascular insufficiency. The disease process can occur in any systemic artery in the human body. For example, atherosclerosis in the arteries that supply the brain (e.g., the carotids, intracerebral, etc.,) can result in stroke. Gangrene may occur when the peripheral arteries are blocked, and coronary artery disease occurs when the arteries that supply oxygen and nutrients to the myocardium are affected. The atherosclerosis process involves lipid-induced biological changes in the arterial walls resulting in a disruption of homeostatic mechanisms that keep the fluid phase of the blood compartment separate from the vessel wall. The atheromatous plaque consists of a mixture of inflammatory and immune cells, fibrous tissue, and fatty material such as low density lipoproteins (LDL). Also, the incidence of atherosclerosis is continuing to increase as a result of the Western diet and the growing proportion of elderly in the population. Additionally, since atherosclerosis is the primary cause of myocardial infarction, cerebral infarction, cerebral apoplexy and so forth, there is a need for its effective prevention and better treatment.

On a given day, the average American consumes about 450 mg of cholesterol and produces an additional 500 to 1,000 mg in the liver and other tissues. Another source of cholesterol is the 500 to 1,000 mg of biliary cholesterol that is secreted into the intestine daily; about 50 percent is reabsorbed. It is well known that the levels of plasma cholesterol have been positively correlated with the incidence of clinical events associated with coronary heart disease as well as atherosclerosis which is characterized by plaque formation. The plaque inhibits blood flow, promotes clot formation and can ultimately cause heart attacks, stroke and claudication.

Elevated serum cholesterol levels (>200 mg/dL) have been indicated as a major risk factor for heart disease, the leading cause of death among Americans. As a result, experts have recommended that those individuals at high risk decrease serum cholesterol levels through dietary changes, a program of physical exercise, and lifestyle changes. It is recommended that the intake of saturated fat and dietary cholesterol be strictly limited and that soluble fiber consumption be increased. Strictly limiting the intake of saturated fat and cholesterol does not, itself, present a risk to proper health and nutrition. Even where saturated fat and cholesterol are severely restricted from the diet, the liver remains able to synthesize sufficient quantities of cholesterol to perform necessary bodily functions.

The regulation of whole-body cholesterol homeostasis in humans and animals involves modulation of cholesterol biosynthesis, bile acid biosynthesis, and the catabolism of the cholesterol-containing plasma lipoproteins. The liver is the main organ responsible for cholesterol biosynthesis and catabolism and, for this reason, it is a prime determinant of plasma cholesterol levels. The liver is the site of synthesis and secretion of very low density lipoproteins (VLDL) which are subsequently metabolized to low density lipoproteins (LDL) in the circulation. LDL are the predominant cholesterol-carrying lipoproteins in the plasma and an increase in their concentration is correlated with increased atherosclerosis.

More recently, experts have begun to examine the individual components of the lipid profile, in addition to the total cholesterol level. While an elevated total cholesterol level is a risk factor, the levels of the various forms of cholesterol which make up total cholesterol may also be risk factors. Elevated low-density lipoprotein (LDL) is a cause for concern, as these loosely packed lipoproteins are more likely to lodge within the cardiovascular system leading to the formation of plaque. Low levels of high-density lipoproteins (HDL) are an additional risk factor, as they serve to sweep artery clogging cholesterol from the blood stream. A better indication of risk appears to be the ratio of total cholesteron:HDL.

Another important factor in determining cholesterol homeostasis is the absorption of cholesterol in the small intestine. On a daily basis, the average human consuming a Western diet eats 300 to 500 mg of cholesterol. In addition, 600 to 1000 mg of cholesterol can traverse the intestines each day. This latter cholesterol is a component of bile and is secreted from the liver. The process of cholesterol absorption is complex and multifaceted. The literature on cholesterol illustrates that approximately 50% of the total cholesterol within the intestinal lumen is absorbed by the cells lining the intestines (i.e., enterocytes). This cholesterol includes both diet-derived and bile- or hepatic-derived cholesterol. Much of the newly-absorbed cholesterol in the enterocytes is esterified by the enzyme acyl-CoA:cholesterol acyltransferase (ACAT). Subsequently, these cholesteryl esters are packaged along with triglycerides and other components (i.e., phospholipids, apoproteins) into another lipoprotein class, chylomicrons.

Chylomicrons are secreted by intestinal cells into the lymph where they can then be transported to the blood. Virtually all of the cholesterol absorbed in the intestines is delivered to the liver by this route. When cholesterol absorption in the intestines is reduced, by whatever means, less cholesterol is delivered to the liver. The consequence of this action is a decreased hepatic lipoprotein (VLDL) production and an increase in the hepatic clearance of plasma cholesterol, mostly as LDL. Thus, the net effect of an inhibition of intestinal cholesterol absorption is a decrease in plasma cholesterol levels.

Several cholesterol-lowering agents were discovered during the 1950s and 1960s. However, most of them had undesirable side effects. The search for a cleaner drug to treat hypercholesterolemia started in he early 1970s. Various experiments on animals and humans had shown that cholesterol could either be absorbed from the diet, or if the diet was lacking sufficient cholesterol to meet the body's needs, then it could be synthesized—mainly in the liver (82%) and the intestine (11%). However, if the diet was rich in cholesterol then synthesis within the body virtually stopped. Previous work had shown that cholesterol production within the body was controlled by a feedback mechanism in which cholesterol inhibited the enzyme 3-hydroxy-3-methylglutaryl-CoA reductase (HMG Co-A reductase). By inhibiting this enzyme, the conversion of HMG-CoA to mevalonic acid was stopped—this step being the key to the body in creating cholesterol. Accordingly, the inhibition of cholesterol biosynthesis by 3-hydroxy-3-methylglutaryl coenzyme A reductase (HMG-CoA) inhibitors (such as the statins family of compounds i.e., mevastatin, lovastatin, pravastatin, fluvastatin, simvastatin, rosuvastatin, cerivastatin and atorvastatin) has been shown to be an effective way to reduce plasma cholesterol and reduce atherosclerosis.

The production of mevalonic acid (a precursor to cholesterol) is brought about when HMG Co-A binds to the enzyme HMG Co-A reductase. After this has occurred, NADPH binds to the enzyme/substrate combination. A reaction then occurs in which NADPH is oxidized to NADP-CoA, and HMG Co-A is reduced to mevalonic acid. As the affinity of HMG Co-A reductase is substantially higher for the statins than it is for HMG Co-A, the statins act as a reversible competitive inhibitor to the enzyme reaction and less mevalonic acid is produced in its presence. Thus the cholesterol production pathway is broken. The introduction of a competitive inhibitor for HMG Co-A reductase results in two physiological responses. In compensation for the inhibition, cells begin to produce more HMG Co-A. The direct reduction in circulating cholesterol is therefore only small. However, the number of low-density lipoprotein (LDL) receptors on hepatocytes increases markedly. As the liver is responsible for removing LDL's (of which cholesterol is a component) from plasma via the LDL receptor mechanism, blood cholesterol levels also fall dramatically.

Plant derived long-chained aliphatic alcohols have also been documented to reduce serum cholesterol levels in experimental models, healthy humans and in type II hypercholesterolemic patients. These aliphatic alcohols, collectively known as policosanol, have been employed in the treatment of elevated serum cholesterol levels in only the past five years, but policosanol has shown much promise, as reported in a number of published human clinical trials. The mechanism of action has not yet been elucidated, but policosanol's effectiveness is attributed to its influence on the bio-synthesis of cholesterol within the liver. This accounts for the ability of policosanol not only to decrease total cholesterol, but also to decrease LDL serum levels and increase HDL levels.

Development of therapeutic agents for the treatment of atherosclerosis and other diseases associated with cholesterol metabolism has been focused on achieving a more complete understanding of the biochemical pathways involved.

Combination therapies of lipid lowering agents have been described previously as having a synergistic hypolipidemic effect. Nevertheless, in practice, many combinations of existing lipid regulating agents are contraindicated, limiting the options of prescribing physicians for patients requiring greater reductions of plasma LDL-cholesterol levels and greater elevations in HDL cholesterol levels. Thus, although there are a variety of hypercholesterolemia therapies, there is a continuing need and a continuing search in this field of art for alternative therapies.

The present invention addresses a long felt need for new medications to further reduce the risk of atherosclerotic disease. This is especially true for patient populations at a higher risk than the population at large, e.g. patients suffering from hypercholesterolemia and hyperlipoproteinemia. The long felt need is addressed by use of combination therapy for reducing cholesterol levels by using a combination of HMG-CoA reductase inhinbitors and compounds that inhibit cholesterol synthesis at a point between the formation of acetate and mevalonate. The prior art is silent regarding combinations of HMG-CoA reductase inhinbitors with policosanol and their use for lowering cholesterol.

OBJECTS OF THE INVENTION

It is an object of the present invention to provide pharmaceutical compositions containing HMG-CoA reductase inhinbitors and compounds that inhibit cholesterol synthesis at a point between the formation of acetate and mevalonate.

It is also an object of the present invention to provide softgel capsules containing HMG-CoA reductase inhinbitors and compounds that inhibit cholesterol synthesis at a point between the formation of acetate and mevalonate.

Still, another object of the invention is to provide a method for reducing serum cholesterol levels in humans and animals by administering a pharmaceutical composition containing a HMG-CoA reductase inhinbitor and a compound that inhibits cholesterol synthesis at a point between the formation of acetate and mevalonate.

A further object of the invention is a pharmaceutical composition containing a HMG-CoA reductase inhinbitor and policosanol.

It is a specific object of the present invention to provide a pharmaceutical composition containing atorvastatin and policosanol.

A still further object of the invention is to provide a softgel capsule containing atorvastatin and policosanol.

Other objects and embodiments of the present invention will be discussed below. However, it is important to note that many additional embodiments of the present invention not described in this specification may nevertheless fall within the spirit and scope of the present invention and/or the claims.

SUMMARY OF THE INVENTION

The present invention is directed to a pharmaceutical composition comprising: (a) an HMG-CoA reductase inhibitor; and (b) a compound that inhibits cholesterol synthesis at a point between the formation of acetate and mevalonate.

The instant invention also provides a softgel capsule comprised of a sheath enclosing a liquid fill, said fill comprising: (a) an effective amount of HMG-CoA reductase inhibitor; and (b) an effective amount of a compound that inhibits cholesterol synthesis at a point between the formation of acetate and mevalonate; and (c) a pharmaceutically acceptable liquid carrier.

The present invention further provides a pharmaceutical formulation for the treatment or prevention of athersclerosis, or for the reduction of plasma cholesterol levels, and suitable for filling softgel capsules comprising: (a) an HMG-CoA reductase inhibitor; (b) a compound that inhibits cholesterol synthesis at a point between the formation of acetate and mevalonate and (c) a carrier comprising polyethylene glycol and glycerine.

The invention further describes a method of treating or preventing atherosclerosis or reducing plasma cholesterol levels comprising simultaneously or sequentially administering to a mammal in need of such treatment or prevention an effective amount of a cholesterol biosynthesis inhibitor selected from the group consisting of HMG CoA reductase inhibitors and a compound that inhibits cholesterol synthesis at a point between the formation of acetate and mevalonate.

The instant invention further provides a method of treating or preventing atherosclerosis or reducing plasma cholesterol levels comprising simultaneously or sequentially administering to a mammal in need of such treatment or prevention an effective amount of atorvastatin and an effective amount of policosanol.

The invention also describes a method for treating a disorder related to elevated serum cholesterol concentration in a mammalian subject, comprising administering to the subject a therapeutically effective amount of a combination of a cholesterol biosynthesis inhibitor selected from the group consisting of HMG CoA reductase inhibitors and a compound that inhibits cholesterol synthesis at a point between the formation of acetate and mevalonate.

The invention also provides a kit comprising in separate containers in a single package pharmaceutical compositions wherein said pharmaceutical compositions are combined to treat or prevent athersclerosis or to reduce plasma cholesterol levels which comprises in one container an effective amount of a cholesterol biosynthesis inhibitor selected from the group consisting of HMG CoA reductase inhibitors in a pharmaceutically acceptable carrier, and in a second container, an effective amount of compound that inhibits cholesterol synthesis at a point between the formation of acetate and mevalonate.

The invention also relates to methods for treating hypercholesterolemia and atherosclerosis, and reducing serum cholesterol in a mammal by administering to a mammal a first amount of a compound which inhibits cholesterol synthesis at a point between the formation of acetate and mevalonate and a second amount of an HMG Co-A reductase inhibitor compound. The first and second amounts together comprise a therapeutically effective amount. Further, the combination therapy can include other active agents for the treatment of hypercholesterolemia, atherosclerosis for reducing serum cholesterol.

The invention further relates to pharmaceutical compositions useful for the treatment of hypercholesterolemia and atherosclerosis, and for reducing serum cholesterol which comprise a combination of a first amount of a compound which inhibits cholesterol synthesis at a point between the formation of acetate and mevalonate and a second amount of an HMG Co-A reductase inhibitor compound. The first and second amounts comprise a therapeutically effective amount. The pharmaceutical compositions of the present invention may optionally contain a pharmaceutically acceptable carrier. Further, the pharmaceutical composition can contain other active agents for the treatment of hypercholesterolemia and atherosclerosis and for reducing serum cholesterol.

The instant invention further provides a method for treating hypercholesterolemia comprising administering to a patient: (a) a first effective amount of policosanol; and (b) a second effective amount of an HMG CoA reductase inhibitor.

DETAILED DESCRIPTION OF THE INVENTION

The present invention is directed to compositions, methods, combinations, and kits for treating a disorder related to elevated serum cholesterol concentration, for example, atherosclerosis, elevated LDL plasma levels, low HDL plasma levels, hypertriglyceridemia, hyperlipidemia, hypertension, hypercholesterolemia, cholesterol gallstones, lipid storage diseases, obesity, and diabetes. The compositions, methods, combinations, and kits of the present invention include pharmaceutical compositions comprising an HMG-CoA reductase inhibitor in combination with a therapeutically effective amount of a compound that inhibits cholesterol synthesis at a point between the formation of acetate and mevalonate.

The present invention thus relates to pharmaceutical combinations comprising a HMG-CoA reductase inhibitor and a compound that inhibits cholesterol synthesis at a point between the formation of acetate and mevalonate wherein the HMG-CoA reductase inhibitor is selected from the group consisting of: mevastatin, lovastatin, pravastatin, fluvastatin, simvastatin, rosuvastatin, cerivastatin and atorvastatin or a pharmaceutically acceptable salt or solvate thereof, or a solvate of such a salt, and the compound that inhibits cholesterol synthesis at a point between the formation of acetate and mevalonate is policosanol.

It is known that HMG-CoA reductase inhibitors and policosanol lower serum cholesterol links by two independent and unrelated mechanisms of action. However, both compounds together are expected to have a synergistic effect on lowering serum cholesterol. As previously mentioned, HMG-CoA reductase inhibitors reduce the conversion of HMG-CoA to mevalonic acid therefore resulting in lower serum cholesterol levels. Policosanol acts directly on the cholesterol synthesis pathway itself, thereby inhibiting the bio-synthesis of cholesterol from saturated fat. However, both compounds together are expected to have a synergistic effect on lowering serum cholesterol levels. Thus, the combination of both HMG-CoA reductase inhibitors and policosanol into a single composition is expected to provide a more effective treatment for elevated serum cholesterol than would be expected from the additive effect of both components.

Mevastatin, lovastatin, pravastatin, fluvastatin, simvastatin, rosuvastatin, cerivastatin and atorvastatin and derivatives and analogs thereof are examples of known as HMG-CoA reductase inhibitors which are used as antihypercholesterolemic agents and which are also useful in making the pharmaceutical combinations of the present invention. The majority of them are produced biotechnologically by fermentation using microorganisms of different species identified as species belonging to *Aspergillus, Monascus, Nocardia, Amycolat psis, Mucor* or *Penicillium* genus, some are obtained by treating the fermentation products using the methods of chemical synthesis, thus leading to semi-synthetic substances, or they are the products of total chemical synthesis. The term HMG-CoA reductase inhibitor is intended to include all pharmaceutically acceptable salt, ester and lactone forms of compounds which have HMG-CoA reductase inhibitory activity, and therefore the use of such salts, esters and lactone forms is included within the scope of this invention.

In the present application, the term "pharmaceutically acceptable salts" shall mean non-toxic salts of the compounds employed in this invention which are generally prepared by reacting the free acid with a suitable organic or inorganic base. Examples of such salts include, but are not limited to benzoate, bicarbonate, sodium, calcium, acetate, laurate, malate, maleate, succinate, tannate, tartrate, benzenesulfonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrobromide, hydrochloride, hydroxynapthoate, iodide, isothionate, lactate, lactobionate, mandelate, mesylate, methylbromide, methylnitrate, methylsulfate, mucate, napsylate, nitrate, oleate, oxalate, pamoate, palmitate, panthothenate, phosphate/diphosphate, polygalacturonate, potassium, salicylate, stearate, subacetate, teoclate, tosylate, and valerate.

As used herein, the phrase "therapeutically effective amount" includes the amount of an HMG-CoA reductase inhibitor (or pharmaceutically acceptable salt thereof), which alone and/or in combination with other drugs i.e., policosanol, provides a benefit in the prevention, treatment, and/or management of one or more conditions or diseases that are associated with high cholesterol and/or high lipid levels or may otherwise benefit from a decrease in blood lipid levels or cholesterol levels. Such conditions or diseases include, but are not limited to, hypercholesterolemia, hyperlipidemia, myocardial infarction, stroke, ischemia, coronary atherosclerosis, coronary death, and/or cardiovascular mortality. In one embodiment, a therapeutically effective amount of atorvastatin and policosanol is the amount required to inhibit or reduce the activity of hepatic 3-hydroxy-3-methylglutaryl-co-enzyme A (HMG-CoA) reductase and to inhibit cholesterol synthesis at a point between the formation of acetate and mevalonate The one or more diseases that can be treated, managed, and/or prevented by the formulations and/or methods of the present invention also include cardiovascular diseases that are not secondary to hypercholesterolemia.

The term "patient" or "subject" includes mammals, especially humans, who take a lipid altering agent for any of the uses described herein. Administration of the lipid altering agent to the subject includes both self-administration and administration to the subject by another person.

The dosage information for HMG-CoA reductase inhibitors is well known in the art, since several are marketed in the U.S. In particular, the daily dosage amounts of the HMG-CoA reductase inhibitor may be the same or similar to those amounts which are employed for antihypercholesterolemic treatment and which are described in the Physicians' Desk Reference (PDR). For example, see the 53$^{rd}$ Ed. of the PDR, 1999 (Medical Economics Co); in particular, see at page 216 the heading "Hypolipidemics," subheading "HMG-CoA Reductase Inhibitors," and the reference pages cited therein. Preferably, the oral dosage amount of HMG-CoA reductase inhibitors is from about 1 to 200 mg/day, and more preferably from about 5 to 160 mg/day. However, dosage amounts will vary depending on the potency of the specific HMG-CoA reductase inhibitor used as well as other factors as noted above. An HMG-CoA reductase inhibitor which has sufficiently greater potency may be given in sub-milligram daily dosages.

As examples, the typical daily dosage amount for atorvastatin may be selected from 10 mg, 20, mg, 40 mg and 80 mg; simvastatin may be selected from 5 mg, 10 mg, 20 mg, 40 mg, and 80 mg; for lovastatin, 10 mg, 20 mg, 40 mg and 80 mg; for fluvastatin sodium, 20 mg, 40 mg and 80 mg; and for pravastatin sodium, 10 mg, 20 mg, and 40 mg. The daily dosage amount for cerivastatin may be in the range of from 0.1 mg to 0.8 mg, and more particularly from 0.2 mg to 0.8 mg, including dosage amounts of 0.2 mg, 0.3 mg, 0.4 mg and 0.8 mg. Oral administration may be in single or divided doses of two, three, or four times daily, although a single daily dose of the HMG-CoA reductase inhibitor is preferred.

The second component of the invention is a compound that that inhibits cholesterol synthesis between the formation of acetate and mevalonate such as a fatty alcohol derived from the wax of sugar cane or from rice bran. A particularly preferred fatty alcohol is policosanol which is a mixture of fatty alcohols derived from the wax of sugar cane. These active substances work to lower cholesterol levels by several mechanisms. It inhibits cholesterol manufacture but does so prior to HMG-CoA reductase. In addition policosanol also exerts exceptional effects on LDL-cholesterol metabolism. Specifically, policosanol increases LDL receptor processing. It exerts this effect by increasing the binding of LDL to its receptor, improving the transport of LDL into the liver cell, and significantly enhancing the breakdown of LDL cholesterol. In addition to lowering LDL, policosanol has also been shown to increase HDL, protect against free radical damage to LDL-cholesterol, and inhibit excessive platelet aggregation. All together, policosanol exerts many pharmacological actions of benefit in the prevention and treatment of atherosclerosis or hardening of the arteries.

A typical pharmaceutical composition of the invention contains from 1% to 99% by weight of an HMG-CoA reductase inhibitor and 1% to 99% by weight of a compound that inhibits cholesterol synthesis between the formation of acetate and mevalonate. A more preferred composition contains 15% to 90% by weight of an HMG-CoA reductase inhibitor and 10% to 85% by weight of a compound that inhibits cholesterol synthesis between the formation of acetate and mevalonate. A most preferred composition contains 40% to 80% by weight of an HMG-CoA reductase inhibitor and 20% to 60% by weight of a compound that inhibits cholesterol synthesis between the formation of acetate and mevalonate.

Typical examples excluding the inert excipients of the pharmaceutical compositions of the invention are outlined in Table 1 below.

TABLE 1

| HMG-CoA reductase inhibitor/amount | Policosanol/amount |
| --- | --- |
| Mevastatin/20 mg | 5 mg |
| Lovastatin/10 mg | 10 mg |
| Pravastatin/20 mg | 5 mg |
| Fluvastatin/20 mg | 15 mg |
| Simvastatin/10 mg | 20 mg |
| Rosuvastatin/10 mg | 10 mg |
| Cerivastatin/0.3 mg | 10 mg |
| Atorvastatin/20 mg | 10 mg |

The compositions are preferably formulated in a unit dosage form. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient. The percentage of the compositions and preparations may, of course, be varied and may conveniently be 100% (application of pure compounds). For example, pharmaceutical compositions according to the invention may contain 0.1%–95% of the therapeutic compositions of this invention, preferably 1%–70%. In any event, the compositions or formulation to be administered will contain a quantity of a compound(s) according to the invention in an amount effective to alleviate the signs of the subject being treated, for example, hypercholesterolemia or atherosclerosis.

The compositions of the invention are typically administered in admixture with suitable pharmaceutical diluents, excipients, or carriers (collectively referred to herein as pharmaceutical carriers) suitably selected with respect to the intended form of administration, that is, oral tablets, capsules, softgel capsules, elixirs, syrups and the like, and consistent with conventional pharmaceutical practices.

For instance, for oral administration in the form of a tablet or capsule, the active drug composition of an HMG-CoA reductase inhibitor and policosanol can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like. For oral administration in liquid form, the oral drug components can be combined with any oral, non-toxic, pharmaceutically acceptable inert carrier such as ethanol, glycerol, water, and the like. Additionally, when desired or necessary, suitable binders, lubricants, disintegrating agents, and coloring agents can also be incorporated into the mixture. Suitable binders include starch, gelatin, natural sugars such as glucose or b-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The precise amount of drug for use in the present compositions will vary depending, for example, on the specific drug combination chosen, the dosage form thereof, i.e., standard versus sustained release, the condition for which the drug is administered and the size and kind of the mammal.

Other components which can be incorporated into the compositions of the instant invention include colorings, flavorings, preservatives, lubricants, flow-enhancers, filling aids, antioxidants, essences, and other aesthetically pleasing components.

In a particular embodiment of the invention, the pharmaceutical compositions of the present invention can be encapsulated within any conventional soft gelatin shell that is capable of substantially containing the composition for a reasonable period of time. The soft gelatin shells of the instant invention can be prepared by combining appropriate amounts of gelatin, water, plasticizer, and any optional components in a suitable vessel and agitating and/or stirring while heating to about 65° C. until a uniform solution is obtained. This soft gelatin shell preparation can then be used for encapsulating the desired quantity of the solubilized fill composition employing standard encapsulation methodology to produce one-piece, hermetically-sealed, soft gelatin capsules.

The solvent system of the invention for filling softgel includes 5% to 45% by weight glycerin, more preferably about 10% to 40% by weight of glycerin and most preferably 15% to 35% with the balance being a solvent such as propylene glycol or other low molecular weight polyethylene glycols. The polyethylene glycols useful herein are those which are liquids at room temperature or have a melting point slightly thereabove. Preferred are the polyethylene glycols having a molecular weight range from about 300 to about 1000 and corresponding n values from about 6 to about 20. More preferred are the polyethylene glycols having a molecular weight range from about 400 to about 1000 and corresponding n values from about 8 to about 20. Most preferred are the polyethylene glycols having a molecular weight range from about 600 to about 1000 and corresponding n values from about 12 to about 20. Most especially preferred is a polyethylene glycol having a molecular weight of about 600 and a corresponding n value of about 12. Liquid and low-melting polyethylene glycols are commercially available from Union Carbide (Danbury, Conn.) under the Carbowax™. See Carbowax™ Polyethylene Glycols.

A particularly preferred fill composition contains the active ingredients (i.e., atorvastatin and policosanol) and a solvent system comprising polyethylene glycol (PEG) and glycerine. The preferred PEG is PEG 400 although other PEGs' of higher or lower molecular weight could be employed.

In a nut shell, the formation of soft gelatin capsules is carried out in a stamping process wherein the capsule wall is assembled from two gelatin halves which are stamped out of a gelatin band and then molded. Preferably, there is utilized the Scherer process operating under the rotary die method. Herein two endless gelatin bands run against two adjacent and mutually counter-rotating molding rollers. While the gelatin bands are being pressed into the molded and so create the capsule halves, the flowable filler is provided into the thus formed capsule through an exact dosing wedge. There follows the sealing together of the capsule halves, their stamping out, a wash procedure for the freeing of attached oil, a rotational dryer step as well as an adjacent shelf drying.

More specifically, the fill formulation of the instant invention is encapsulated into one-piece gelatin sheath or shell that includes a plasticizer to control the softness and flexibility of the sheath, water, and optionally, other additives, such as flavorants, colorants, opacifiers, etc. The softgel capsules may be produced in a known manner with a rotary die process in which a molten mass of a gelatin sheath formulation is fed from a reservoir onto drums to form two spaced sheets or ribbons of gelatin in a semi-molten state. These ribbons are fed around rollers and brought together at a convergent angle into the nip of a pair of roller dies that include opposed die cavities. A fill formulation to be encapsulated is fed into the wedge-shaped joinder of the ribbons.

The gelatin ribbons are continuously conveyed between the dies, with portions of the fill formulation being trapped between the sheets inside the die cavities. The sheets are then pressed together, and severed around each die so that opposed edges of the sheets flow together to form a continuous gelatin sheath around the entrapped medicament. The part of the gelatin sheet that is severed from the segments forming the capsules is then collected for recycling, and the soft capsules are dried.

Various sheath formulations known in the prior art may be used to encapsulate the fill formulations of the present invention. For example, suitable sheath formulations may include from about 30 to about 50% by weight gelatin; at least 18% by weight, and preferably up to about 40% by weight, of a plasticizer; and from about 20 to about 50% by weight water. These formulations, when formed into capsules and dried, will result in capsule sheaths comprised of from about 40 to about 75% by weight gelatin; from about 18% to about 40% by weight plasticizer; and from about 5 to about 15% by weight water.

The gelatin will normally have a bloom in the range of from about 140 to about 280, and may be Type A or B gelatins or a mixture thereof. Limed bone, acid bone, fish and/or pig skin gelatins may be used.

The gelatin capsules are formed into the desired shape and size so that they can be readily swallowed. The soft gelatin capsules of the instant invention are of a suitable size for easy swallowing and typically contain from about 1 mg to about 100 mg of the pharmaceutical active composition. Soft gelatin capsules and encapsulation methods are described in P. K. Wilkinson et al., "Softgels: Manufacturing Considerations", Drugs and the Pharmaceutical Sciences, 41 (Specialized Drug Delivery Systems), P. Tyle, Ed. (Marcel Dekker, Inc., New York, 1990) pp. 409–449; F. S. Hom et al., "Capsules, Soft" Encyclopedia of Pharmaceutical Technology, vol. 2, J. Swarbrick and J. C. Boylan, eds. (Marcel Dekker, Inc., New York, 1990) pp. 269–284; M. S. Patel et al., "Advances in Softgel Formulation Technology", Manufacturing Chemist, vol. 60, no. 7, pp. 26–28 (July 1989); M. S. Patel et al., "Softgel Technology", Manufacturing. Chemist, vol. 60, no. 8, pp. 47–49 (August 1989); R. F. Jimerson, "Softgel (Soft Gelatin Capsule) Update", Drug Development and Industrial Pharmacy (Interphex '86 Conference), vol. 12, no. 8 & 9, pp. 1133–1144 (1986); and W. R. Ebert, "Soft Elastic Gelatin Capsules: A Unique Dosage Form", Pharmaceutical Technology, vol. 1, no. 5, pp. 44–50 (1977); these references are incorporated by reference herein in their entirety. The resulting soft gelatin capsule is soluble in water and in gastrointestinal fluids. Upon swallowing the capsule, the gelatin shell rapidly dissolves or ruptures in the gastrointestinal tract thereby introducing the pharmaceutical actives into the physiological system.

In practicing the methods of the invention, combination therapy refers to administration of a first effective amount of an HMG Co-A reductase inhibitor compound and a second effective amount of a compound that inhibits cholesterol synthesis at a point between the formation of acetate and mevalonate and/or other active agent to treat hypercholesterolemia and atherosclerosis, and reduce serum cholesterol. Administration in combination therapy encompasses co-administration of the first and second amounts of the compounds of the combination therapy in a single substantially simultaneous manner, such as in a single capsule or tablet having a fixed ratio of first and second amounts, or in multiple, separate capsules or tablets for each. In addition, such administration also encompasses use of each compound in a sequential manner.

The dosage regimen to treat hypercholesterolemia and atherosclerosis and reduce plasma cholesterol with the combination therapy and pharmaceutical compositions of the present invention is selected in accordance with a variety of factors. These include the type, age, weight, sex, diet, and medical condition of the patient, the severity of the disease, the route of administration, pharmacological consideration such as the activity, efficacy, pharmacokinetics and toxicology profiles of the particular compound employed, whether a drug delivery system is utilized, and whether the compound is administered as part of a drug combination. Thus, the dosage regimen actually employed may vary widely and therefore deviate from the preferred dosage regimen set forth above.

Initial treatment of a patient suffering from a hyperlipidemic condition such as hypercholesterolemia and atherosclerosis can begin with the dosages indicated above. Treatment should generally be continued as necessary over a period of several weeks to several months or years until the condition has been controlled or eliminated. Patients undergoing treatment with the compounds or compositions disclosed herein can be routinely monitored by, for example, measuring serum LDL and total cholesterol levels by any of the methods well known in the art, to determine the effectiveness of the combination therapy. Continuous analysis of such data permits modification of the treatment regimen during therapy so that optimal effective amounts of each type of agent are administered at any point in time, and so that the duration of treatment can be determined as well. In this way, the treatment regimen/dosing schedule can be rationally modified over the course of therapy so that the lowest amount of policosanol and HMG Co-A reductase inhibitor, which together exhibit therapeutic effectiveness, is administered and so that administration is continued only so long as is necessary to successfully to treat the hyperlipidemic condition such as hypercholesterolemia and atherosclerosis.

A potential advantage of the combination therapy disclosed herein may be reduction of the amount of policosanol, HMG Co-A reductase inhibitor, and/or other active agent, or all effective in treating hyperlipidemic conditions such as atherosclerosis and hypercholesterolemia, and in reducing serum cholesterol.

In the case of HMG Co-A reductase inhibitors, the dose can range from about 0.01 mg to about 500 mg, more particularly from about 0.10 mg to about 250 mg, most particularly from about 1 mg to about 100 mg/day, for example, from about 5 mg to about 80 mg/day or any other dose, dependent upon the specific inhibitor, as is known in the art. Suitable dose ranges for treatment with an HMG Co-A reductase inhibitor are available in the Physician's Desk Reference and the Merck Index (Twelfth Edition), the contents of which are incorporated by reference. The policosanol can be administered in an amount from about 1 mg/day to about 30 mg/day, preferably from about 3 mg/day to about 25 mg/day, more preferably from about 5 mg/day to about 20 mg/day, and most preferably from about 10 mg/day to about 20 mg/kg/day.

The first and second amounts of the compounds of the combination therapy can be administered by any dual combination of oral/oral or oral/parenteral route.

The particular dosage will depend on the individual patient (e.g., the patient's weight and the extent of bile salt removal required). The pharmaceutical combination of the invention can be administered either in many forms, and can be flavored or added to a food or drink, if desired, to enhance patient acceptability. Additional ingredients such as other drugs for treating hypercholesterolemia, atherosclerosis or other related indications, or inert ingredients, such as artificial coloring agents can be added as well.

Examples of suitable forms for administration include pills, tablets, capsules, and powders (e.g., for sprinkling on food). The pill, tablet, capsule, or powder can be coated with a substance capable of protecting the composition from disintegration in the esophagus but will allow disintegration of the composition in the stomach and mixing with food to pass into the patient's small intestine. The polymer can be administered alone or in combination with a pharmaceutically acceptable carrier, diluent or excipient substance, such as a solid, liquid or semi-solid material. Examples of suitable carriers, diluents and excipients include lactose, dextrose, sucrose, sorbitol, mannitol, starches, gum acacia, alginates, tragacanth, gelatin, calcium silicate, cellulose e.g., magnesium carbonate or a phospholipid with which the polymer can form a micelle.

The following examples further describe and demonstrate embodiments within the scope of the present invention. The examples are given solely for the purpose of illustration and are not to be construed as limitations of the present invention, as many variations thereof are possible without departing from the spirit and scope of the invention.

EXAMPLES

The following procedure is used throughout the examples below to dissolve the active principle in the solvent system which is then encapsulated in the softgel.

Mix the PEG 400 and the Glycerin under moderate agitation, heat to a temperature ranging from 55° C.+/−5° C. Add the active components and strongly mix to have a good dispersion. The mixture is then strongly agitated until a clear transparent solution is obtained. Stop the heating and keep agitating the solution until it is at room temperature. The active material solution is suitable to be encapsulated in soft gelatin capsules.

EXAMPLE 1

| COMPONENTS | AMOUNT/mg |
| --- | --- |
| Atorvastatin | 10 mg |
| Policosanol | 10 mg |
| Glycerin | 20 mg |
| PEG 400 | 60 mg |
| Total | 100 mg |

EXAMPLE 2

| COMPONENTS | AMOUNT/mg |
| --- | --- |
| Mevastatin | 20 mg |
| Policosanol | 10 mg |
| Glycerin | 20 mg |
| PEG 400 | 60 mg |
| Total | 110 mg |

EXAMPLE 3

| COMPONENTS | AMOUNT/mg |
| --- | --- |
| Lovastatin | 10 mg |
| Policosanol | 10 mg |
| Glycerin | 20 mg |
| PEG 400 | 60 mg |
| Total | 110 mg |

EXAMPLE 4

| COMPONENTS | AMOUNT/mg |
| --- | --- |
| cerivastatin | 0.4 mg |
| Policosanol | 10 mg |
| Glycerin | 20 mg |
| PEG 400 | 60 mg |
| Total | 90.4 mg |

EXAMPLE 5

| COMPONENTS | AMOUNT/mg |
| --- | --- |
| simvastatin | 20 mg |
| Policosanol | 10 mg |
| Glycerin | 20 mg |
| PEG 400 | 60 mg |
| Total | 110 mg |

EXAMPLE 6

| COMPONENTS | AMOUNT/mg |
| --- | --- |
| pravastatin | 15 mg |
| Policosanol | 5 mg |
| Glycerin | 20 mg |
| PEG 400 | 60 mg |
| Total | 100 mg |

EXAMPLE 7

| COMPONENTS | AMOUNT/mg |
| --- | --- |
| fluvastatin | 10 mg |
| Policosanol | 5 mg |
| Glycerin | 20 mg |
| PEG 400 | 60 mg |
| Total | 95 mg |

EXAMPLE 8

| COMPONENTS | AMOUNT/mg |
| --- | --- |
| rosuvastatin | 10 mg |
| Policosanol | 10 mg |
| Glycerin | 20 mg |
| PEG 400 | 60 mg |
| Total | 100 mg |

EXAMPLE 9

Soft Gelatin Capsule Containing a solubilized Composition
A soft gelatin mixture is first prepared from the following ingredients.

| INGREDIENT | WEIGHT % |
|---|---|
| Gelatin | 48.00 |
| Glycerin | 14.00 |
| Water | QS 100 | the above ingredients are combined in a suitable vessel and heated with mixing at about 65° C. to form a uniform solution. Using standard encapsulation methodology, the resulting solution is used to prepare soft gelatin capsules containing approximately 100 mg of the composition as prepared in Example 1. The resulting soft gelatin capsules are suitable for oral administration.

All patents, patent applications and publications cited in this application are hereby incorporated by reference in their entirety for all purposes to the same extent as if each individual patent, patent application or publication were so individually denoted.

While the many embodiments of the invention have been disclosed above and include presently preferred embodiments, many other embodiments and variations are possible within the scope of the present disclosure and in the appended claims that follow. Accordingly, the details of the preferred embodiments and examples provided are not to be construed as limiting. It is to be understood that the terms used herein are merely descriptive rather than limiting and that various changes, numerous equivalents may be made without departing from the spirit or scope of the claimed invention.

What is being claimed is:

1. A pharmaceutical composition comprising:
    (a) an effective amount of HMG-CoA reductase inhibitor; and
    (b) an effective amount of a compound that inhibits cholesterol synthesis at a point between the formation of acetate and mevalonate.

2. The pharmaceutical composition of claim 1 wherein said HMG-CoA reductase inhibitor is selected from the group consisting of mevastatin, lovastatin, pravastatin, fluvastatin, simvastatin, rosuvastatin, cerivastatin and atorvastatin and the pharmaceutically acceptable salts, esters, lactones and isomeric forms thereof.

3. The pharmaceutical composition of claim 1 wherein said compound that inhibits cholesterol synthesis between the formation of acetate and mevalonate is a $C_{20}$–$C_{39}$ fatty alcohol and mixtures thereof.

4. The pharmaceutical composition of claim 3 wherein said compound that inhibits cholesterol synthesis between the formation of acetate and mevalonate is a $C_{22}$–$C_{38}$ fatty alcohol and mixtures thereof.

5. The pharmaceutical composition of claim 4 wherein said compound that inhibits cholesterol synthesis between the formation of acetate and mevalonate is policosanol.

6. The pharmaceutical composition of claim 1 wherein said HMG-CoA inhibitor is atorvastatin and said compound that inhibits cholesterol synthesis between the formation of acetate and mevalonate is policosanol.

7. The pharmaceutical composition of claim 1 wherein said HMG-CoA inhibitor is lovastatin and said compound that inhibits cholesterol synthesis between the formation of acetate and mevalonate is policosanol.

8. The pharmaceutical composition of claim 1 wherein said HMG-CoA inhibitor is pravastatin, and said compound that inhibits cholesterol synthesis between the formation of acetate and mevalonate is policosanol.

9. The pharmaceutical composition of claim 1 wherein said HMG-CoA inhibitor is fluvastatin and said compound that inhibits cholesterol synthesis between the formation of acetate and mevalonate is policosanol.

10. The pharmaceutical composition of claim 1 wherein said HMG-CoA inhibitor is simvastatin and said compound that inhibits cholesterol synthesis between the formation of acetate and mevalonate is policosanol.

11. A softgel capsule comprised of a sheath enclosing a liquid fill, said fill comprising:
    (a) an effective amount of HMG-CoA reductase inhibitor; and
    (b) an effective amount of a compound that inhibits cholesterol synthesis at a point between the formation of acetate and mevalonate; and
    (3) a pharmaceutically acceptable liquid carrier.

12. The softgel capsule of claim 11, wherein said HMG-CoA reductase inhibitor is atorvastatin and said compound that inhibits cholesterol synthesis at a point between the formation of acetate and mevalonate is policosanol.

13. A pharmaceutical formulation for the treatment of atherosclerosis, or for the reduction of plasma cholesterol levels, and suitable for filling softgel capsules comprising:
(a) an effective amount of an HMG-CoA reductase inhibitor;
(b) an effective amount of a compound that inhibits cholesterol synthesis at a point between the formation of acetate and mevalonate and (c) a carrier comprising polyethylene glycol and glycerine.

14. The pharmaceutical formulation of claim 13 wherein said HMG-CoA reductase inhibitor is atorvastatin and said compound that inhibits cholesterol synthesis at a point between the formation of acetate and mevalonate is policosanol.

15. The pharmaceutical formulation of claim 13 wherein said HMG-CoA reductase inhibitor is mevastatin and said compound that inhibits cholesterol synthesis at a point between the formation of acetate and mevalonate is policosanol.

16. The pharmaceutical formulation of claim 13 wherein said HMG-CoA reductase inhibitor is cerivastatin and said compound that inhibits cholesterol synthesis at a point between the formation of acetate and mevalonate is policosanol.

17. The pharmaceutical formulation of claim 13 wherein said HMG-CoA reductase inhibitor is lovastatin and said compound that inhibits cholesterol synthesis at a point between the formation of acetate and mevalonate is policosanol.

18. The pharmaceutical formulation of claim 13 wherein said HMG-CoA reductase inhibitor is pravastatin and said compound that inhibits cholesterol synthesis at a point between the formation of acetate and mevalonate is policosanol.

19. The pharmaceutical formulation of claim 13 wherein said HMG-CoA reductase inhibitor is fluvastatin and said compound that inhibits cholesterol synthesis at a point between the formation of acetate and mevalonate is policosanol.

20. The pharmaceutical formulation of claim 13 wherein said HMG-CoA reductase inhibitor is rosuvastatin and said compound that inhibits cholesterol synthesis at a point between the formation of acetate and mevalonate is policosanol.

21. A kit comprising in separate containers in a single package pharmaceutical compositions wherein said pharmaceutical compositions are combined to treat athersclerosis or to reduce plasma cholesterol levels which comprises in one container an effective amount of a cholesterol biosynthesis inhibitor selected from the group consisting of HMG CoA reductase inhibitors in a pharmaceutically acceptable carrier, and in a second container, an effective amount of compound that inhibits cholesterol synthesis at a point between the formation of acetate and mevalonate.

22. A method for treating a disorder related to elevated serum cholesterol concentration in a mammalian subject, comprising administering to the subject a therapeutically effective amount of a combination of a cholesterol biosynthesis inhibitor selected from the group consisting of HMG CoA reductase inhibitors and a compound that inhibits cholesterol synthesis at a point between the formation of acetate and mevalonate, wherein said combination includes (a) at least one inhibitor of HMG CoA reductase and (b) a compound that inhibits cholesterol synthesis at a point between the formation of acetate and mevalonate.

23. The method of claim 22 wherein said HMG-CoA reductase inhibitor is selected from the group consisting of mevastatin, lovastatin, pravastatin, fluvastatin, simvastatin, rosuvastatin, cerivastatin and atorvastatin and said compound that inhibits cholesterol synthesis at a point between the formation of acetate and mevalonate is policosanol.

24. A method for treating hypercholesterolemia comprising administering to a patient:
   (a) a first effective amount of policosanol; and
   (b) a second effective amount of an HMG CoA reductase inhibitor.

* * * * *